United States Patent [19]

Steer et al.

[11] Patent Number: 5,178,615
[45] Date of Patent: Jan. 12, 1993

[54] OSTOMY BAG COUPLING

[75] Inventors: Peter L. Steer, Reigate; Neil P. Wiltshire, Lingfield, both of England

[73] Assignee: E. R. Squibb & Sons, Inc., Princeton, N.J.

[21] Appl. No.: 365,410

[22] Filed: Jun. 13, 1989

[30] Foreign Application Priority Data

Jun. 13, 1988 [GB] United Kingdom ............... 8813967
Jun. 13, 1988 [GB] United Kingdom ............. 8817995.7

[51] Int. Cl.⁵ ............................................. A61F 5/44
[52] U.S. Cl. ................................... 604/338; 604/342
[58] Field of Search .......................... 604/336–339, 604/341, 342, 314, 332–335, 340, 343, 345; 220/293, 301, 302; 215/317, 332

[56] References Cited

U.S. PATENT DOCUMENTS

| 3,736,934 | 4/1973 | Hennessy | 604/342 |
| 4,460,363 | 7/1984 | Steer et al. | 604/336 |
| 4,820,285 | 4/1989 | Leise et al. | 604/339 |
| 4,834,732 | 5/1989 | Steer et al. | 604/342 |
| 4,892,530 | 1/1990 | Steer | 604/338 |
| 4,931,045 | 6/1990 | Steer | 604/338 |
| 5,041,102 | 8/1991 | Steer et al. | 604/338 |

FOREIGN PATENT DOCUMENTS

| 0135269 | 3/1985 | European Pat. Off. | |
| 0150276 | 8/1985 | European Pat. Off. | 604/332 |
| 3417183 | 5/1984 | Fed. Rep. of Germany . | |
| 8503427 | 8/1985 | PCT Int'l Appl. | |
| 1099455 | 1/1965 | United Kingdom . | |
| 1021145 | 3/1966 | United Kingdom . | |
| 1568860 | 6/1980 | United Kingdom . | |
| 1579875 | 11/1980 | United Kingdom . | |
| 2121902 | 3/1982 | United Kingdom . | |
| 2163350 | 2/1986 | United Kingdom | 604/338 |
| 2177926 | 2/1987 | United Kingdom . | |
| 2179556 | 3/1987 | United Kingdom | 604/332 |
| 2183481 | 6/1987 | United Kingdom . | |
| 2193097 | 2/1988 | United Kingdom | 604/332 |
| 2193098 | 2/1988 | United Kingdom . | |
| 2201345 | 9/1988 | United Kingdom . | |
| 2201346 | 9/1988 | United Kingdom . | |

Primary Examiner—Randall L. Green
Assistant Examiner—R. Clarke
Attorney, Agent, or Firm—Stuart E. Krieger

[57] ABSTRACT

An ostomy bag coupling appliance has body side and bag side couplings each including a seal means. The bag side coupling includes one ring like member carrying the seal means associated with a locking ring which can be rotated relative to the member. The locking ring and the body side coupling have interengaging parts whereby upon relative rotational movement (about the axis of the coupling) these cooperating parts can be engaged and disengaged so locking together, or allowing to be released, as the case may be, the body side and bag side couplings.

19 Claims, 4 Drawing Sheets

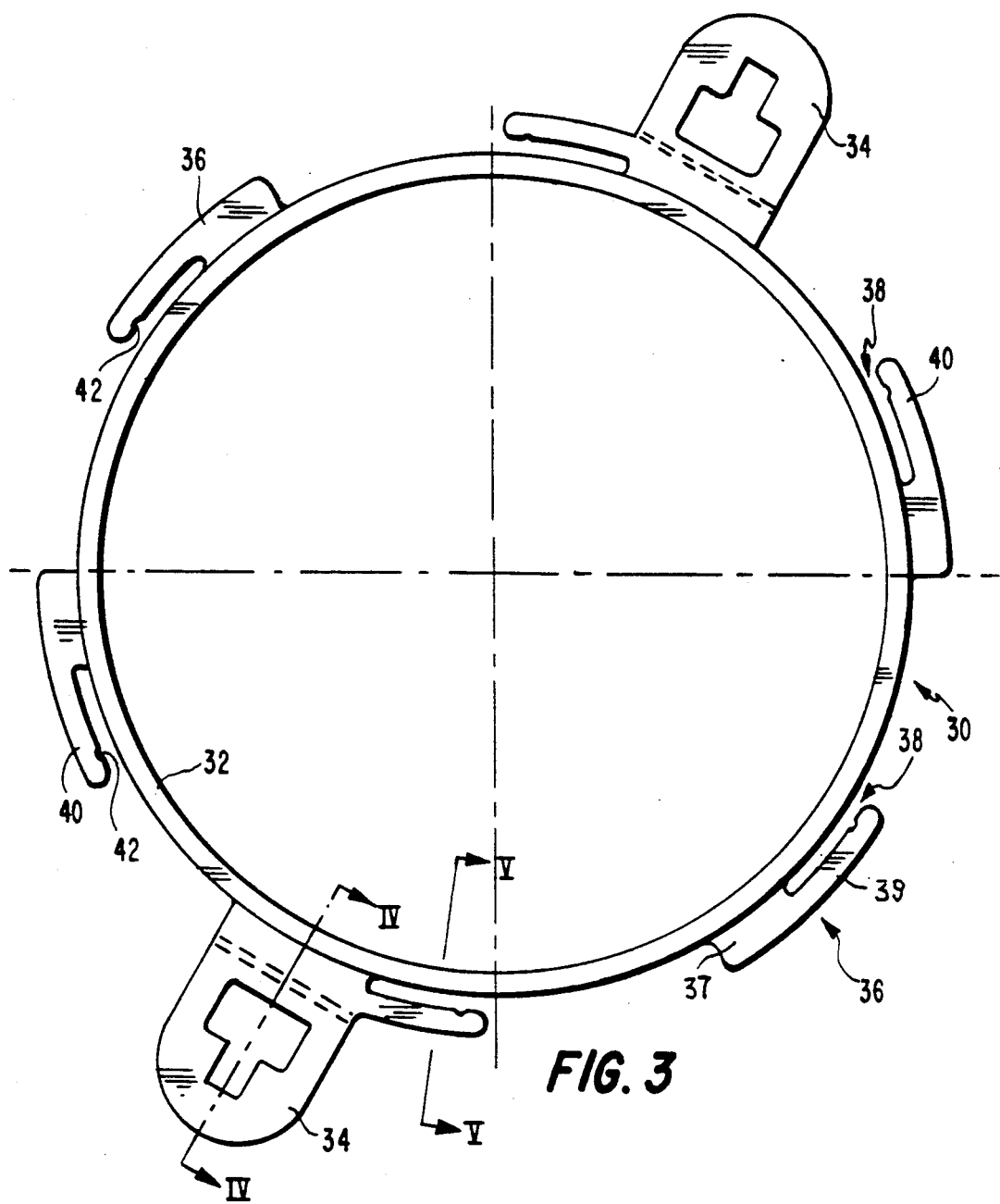
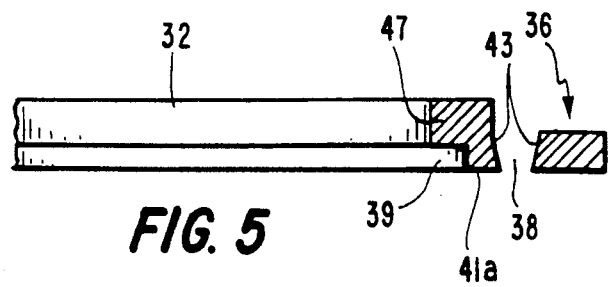
FIG. 3
FIG. 4
FIG. 5

OSTOMY BAG COUPLING

BACKGROUND OF THE INVENTION

This invention relates to an ostomy bag coupling for allowing coupling and uncoupling of an ostomy bag from the user's body.

A typical form of ostomy bag coupling comprises a body side coupling which is fixed to the body of the user by a medical adhesive, and a bag side coupling which is attached to a bag. The bag side coupling is releasably attached to the body side coupling, so that a bag may be replaced simply, without requiring removal of the body side coupling from the body. It will be appreciated that it is important to ensure the accidental uncoupling during use is minimized to maximize the confidence of the user.

In U.K. Patent No. 1,579,875, there is disclosed an ostomy bag coupling in which the body side coupling and the bag side coupling can be locked together to prevent accidental separation. In this arrangement, the bag side coupling has a coupling part of continuous channel section which effectively braces the coupling against the flexing movements to which it will be subjected to in use. This means that the user will experience discomfort as the body side coupling will tend to resist any flexing movement of the area of the body to which the coupling is attached. Also, the increased stiffness will mean that the coupling may not naturally conform to the local area of the user's body and thus attachment of the body side coupling to the body may require special care. Furthermore, the coupling of U.K. Patent No. 1,579,875, projects a significant distance when attached to the user's body, so that the coupling may be visible when the user is wearing light clothing.

SUMMARY OF THE INVENTION

The illustrated embodiment of an ostomy bag coupling according to the present invention, provides a lockable ostomy bag coupling which is of low profile and allows a degree of flexure with the user's body.

According to one aspect of this invention, there is provided an ostomy bag coupling including a body side coupling which includes a first seal means surrounding an inlet or stoma aperture and body side support means supporting said first seal means, and a bag side coupling which includes second seal means for cooperating with said first seal means and a bag side support means associated with said second seal means, one of said body side and bag side support means including, at a plurality of locations spaced therearound, spurs defining respective generally circumferential slots and the other support means including a plurality of spaced upstanding projections releasably receivable in said slots, whereby on engagement of said first and second seal means and subsequent relative rotation of said support means in the appropriate sense, said projections are received in respective slots thereby releasably locking the coupling against separating movement.

The invention will be better understood from the following description of a non-limiting example of an ostomy bag coupling according to the invention, reference being made to the accompanying drawings, in which like parts are denoted by like numerals, and in which:

BRIEF DESCRIPTION OF THE DRAWINGS

FIG. 3 is a top plan view of the locking ring of the bag side coupling for releasable locking attachment to the body side coupling of FIG. 1;

FIG. 4 is a fragmentary section on lines IV—IV of FIG. 3;

FIG. 5 is a fragmentary section on an enlarged scale on lines V—V of FIG. 3;

DETAILED DESCRIPTION OF THE DRAWINGS

Figure 1:
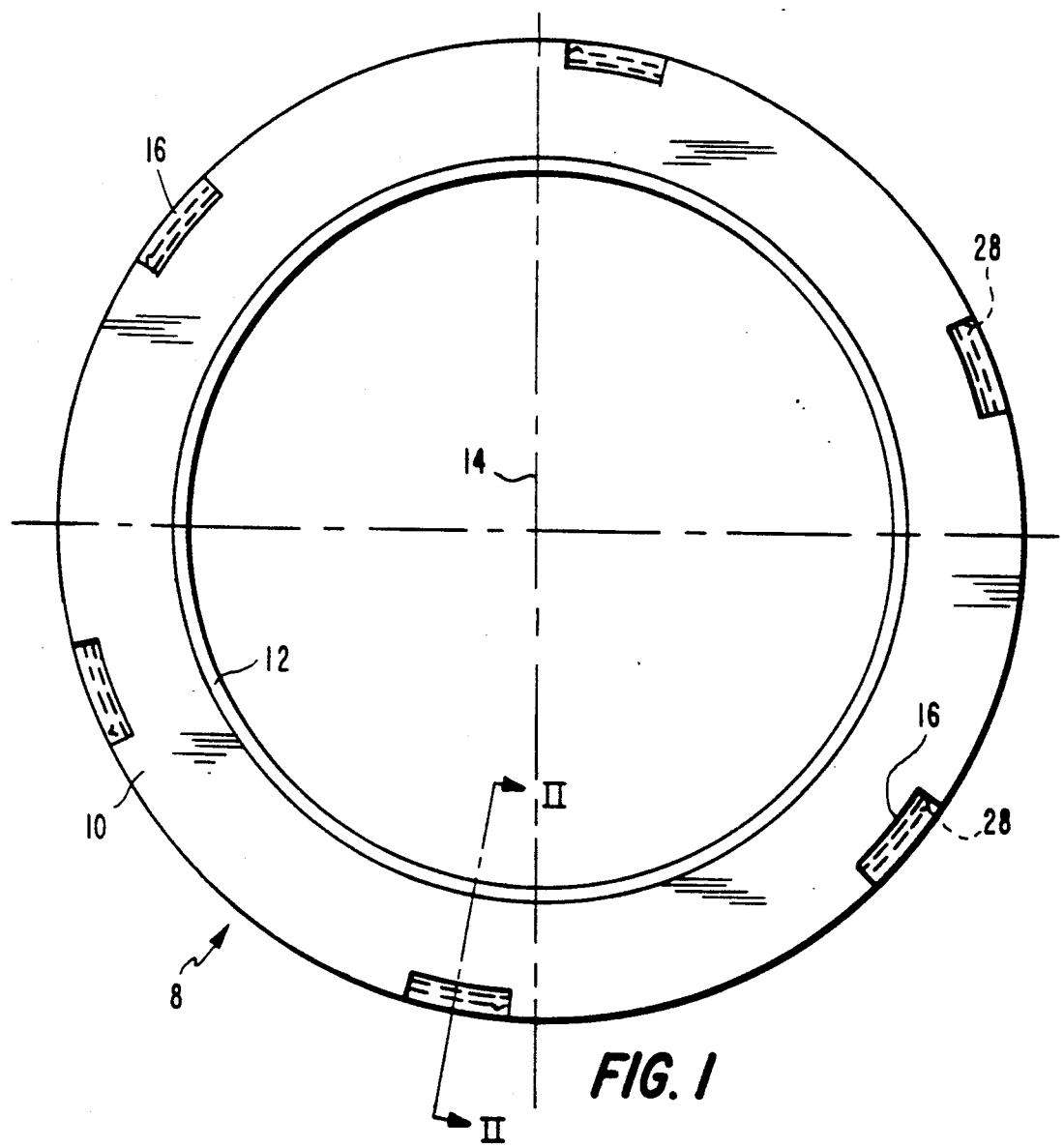
FIG. 1 is a top plan view of a body side coupling of an exemplary ostomy bag coupling.
Figure 2:
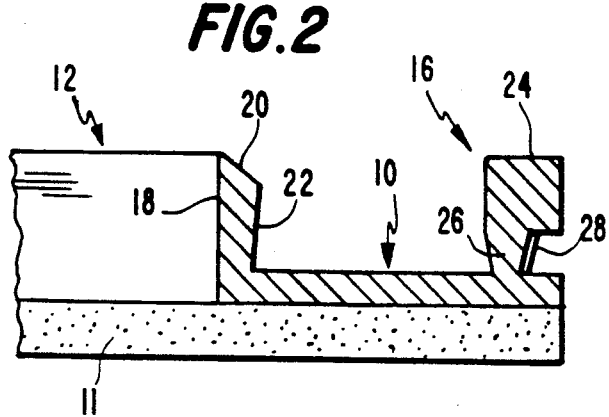
FIG. 2 is a fragmentary section on lines II—II of FIG. 1.

Referring to FIGS. 1 and 2, the body side coupling 8 is integrally molded from a synthetic plastics material, e.g. low density polyethylene material and comprises a thin annular flange 10, a chute 12 upstanding from the flange 10 and surrounding an inlet or stoma aperture 14, and six equispaced projections 16 upstanding from the outer periphery of the flange. The inner surface 18 of the chute 12 is cylindrical but the outer surface comprises a chamfered portion 20 and a tapered portion 22 which converges towards the flange. The tapered portion 22 is herein referred to as a first seal means and assists in maintaining a seal, as to be described below.

Each of the locking projections 16 is generally arcuate as seen in plan and comprises an enlarged head portion 24 connected to the surface of the flange by a tapered V-portion 26. The radially outer surface of each V-portion 26 includes a detent pip 28 for engaging an associated recess in a locking ring 30 of a bag side coupling as will be described below.

The lower surface of the flange 10 includes a suitable medical grade adhesive layer 11 which causes the body side coupling to adhere to the body of the user. An example of a suitable material is that known as "STOMAHESIVE" (Registered Trade Mark) which comprises a sheet of plastic adhesive material comprising a blend of a water soluble or a water swellable hydrocolloid and a water insoluble viscous elastic binder. Further details are disclosed in U.K. Patent No. 1,088,992.

Figure 6:
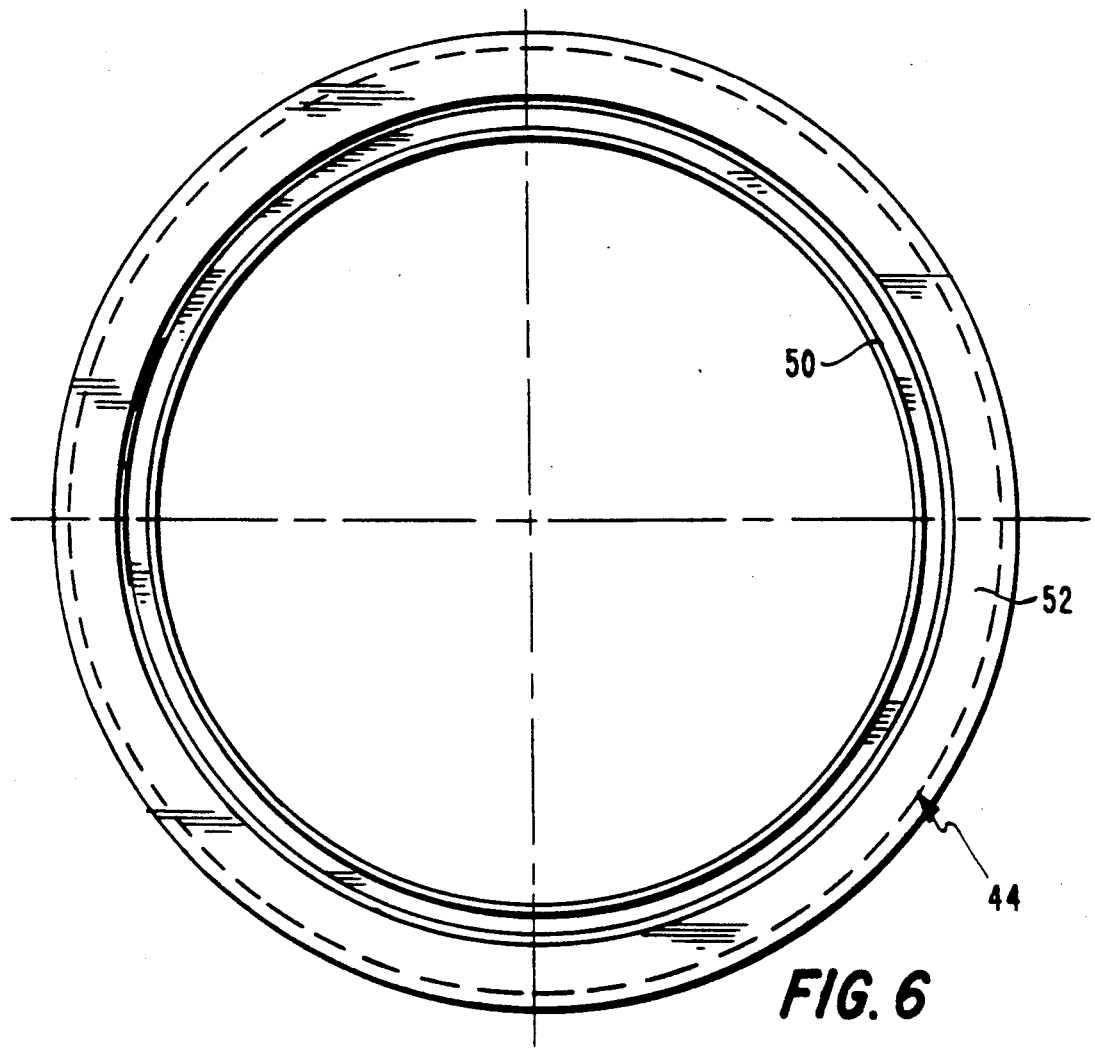
FIG. 6 is a top plan view of the seal ring of the bag side coupling.
Figure 7:
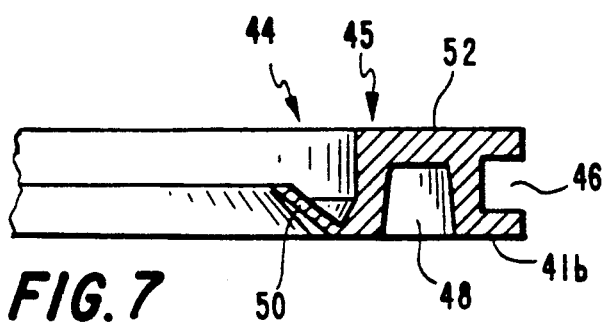
FIG. 7 is a fragmentary section through the seal ring.

The bag side coupling includes two separately formed parts: a locking ring 30 (FIGS. 3 to 5) and a seal ring 44 (FIGS. 6 and 7). Together the seal ring 44 and locking ring 30 are also herein referred to as a bag side support means. Referring initially to FIGS. 3 to 5, the locking ring 30 is formed of a synthetic plastics material, e.g. an engineering plastics material and comprises a ring portion 32, a pair of diametrically opposed lugs 34, and six equispaced locking spurs 36 extending from the outer periphery of the locking ring. The lugs may be gripped to rotate the ring 30 when locking and unlocking the coupling. They serve, if required, to attach the coupling to a belt. The inner surface of the locking ring 30 is stepped at 39 to accommodate the seal ring so that their lower surfaces 41a and 41b are flush (see FIG. 8). The locking spurs 36 are generally arcuate and each locking spur includes a base portion 37 connected to the ring portion 32 and an elongated portion 39 extending generally circumferentially and spaced apart from the ring portion 32. The inner surfaces of the elongated portions 39, together with the opposed surfaces of the ring portion 32, define respective circumferential slots 38.

The walls 43 of the slot 38 diverge upwardly (as seen in FIG. 5) to be complimentarily shaped to the V-portion 26 of the locking projections 16. In the end region 40 of each spur 36, the spur diminishes in axial thickness towards the free end. This tapered lead-in assists engagement of the projections 16 and the slots 38 during the coupling operation. The radially inner surface of each end region also includes a recess 42 for receiving the pip 28 of the associated projection 16 to provide a detent action.

Figure 8:
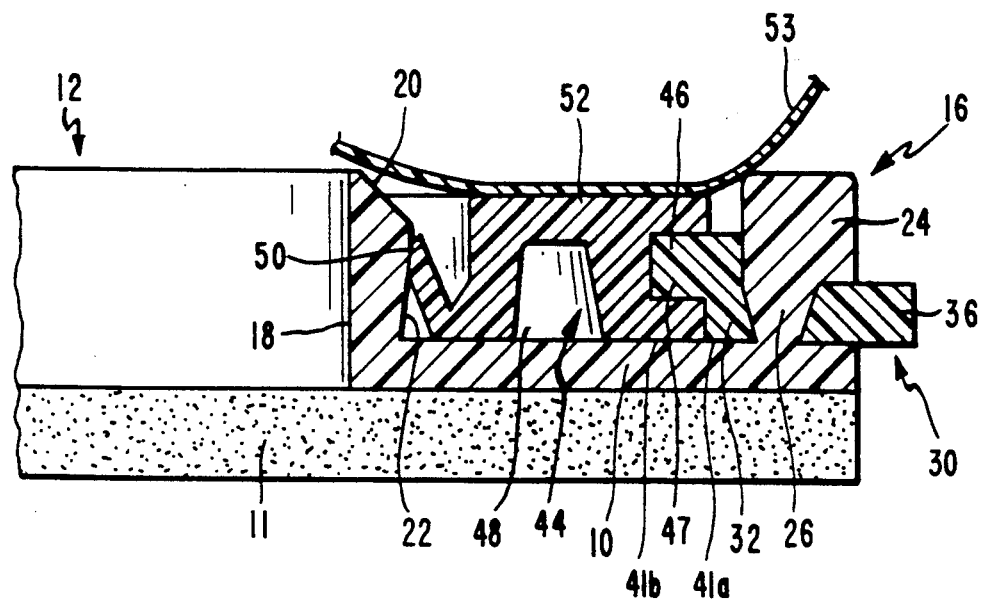
FIG. 8 is a fragmentary section through the coupling when assembled and locked.

Referring now to FIGS. 6-8, the seal ring 44 is formed of a synthetic plastics material, e.g. EVA material and includes an outer main body portion 45 having a recess 46 (FIG. 7) extending around the outer circumference for receiving a radially inner portion 47 of the locking ring 30 (see FIG. 8). The ring 44 also has, optionally, an annular recess 48. A flexible and deflectible annular seal lip 50 projects inwardly from the inner periphery of the main body portion 45. The wall 53 surrounding the stomal orifice of the ostomy bag is attached to a radially extending surface 52 of the main body portion of the seal ring 44 by suitable means, e.g. welding or adhesive. The seal lip 50 is an example of a seal means herein referred to as a second seal means.

In manufacture, the body side coupling 8 is formed and a layer 11 of adhesive applied to the lower side of the flange 10. The locking ring 30 and the seal ring 44 are separately formed and the ostomy bag is secured to the seal ring 44.

In use the wearer attaches the body side coupling 8 to his/her peristomal area and then attaches the bag side coupling by maneuvering the bag side coupling relative to the body side coupling so that the projections 16 and the spurs 36 are out of registration. The bag side coupling is then pushed in an axial direction towards the other couplings so that the seal lip 50 deforms to ride over the chamfered out surface 20 of the chute 12 to engage the tapered portion 22. In this position, the flush lower surfaces 41a and 41b of the locking ring 30 and the seal ring 44, respectively, engage or are spaced closely from the upper surface of the flange 10. The interaction of the seal lip 50 and the tapered portion 22 provides a generally axial bias force tending to urge the locking ring 30 and the seal ring 44 against the flange 10 and the portions 24.

Figure 9:
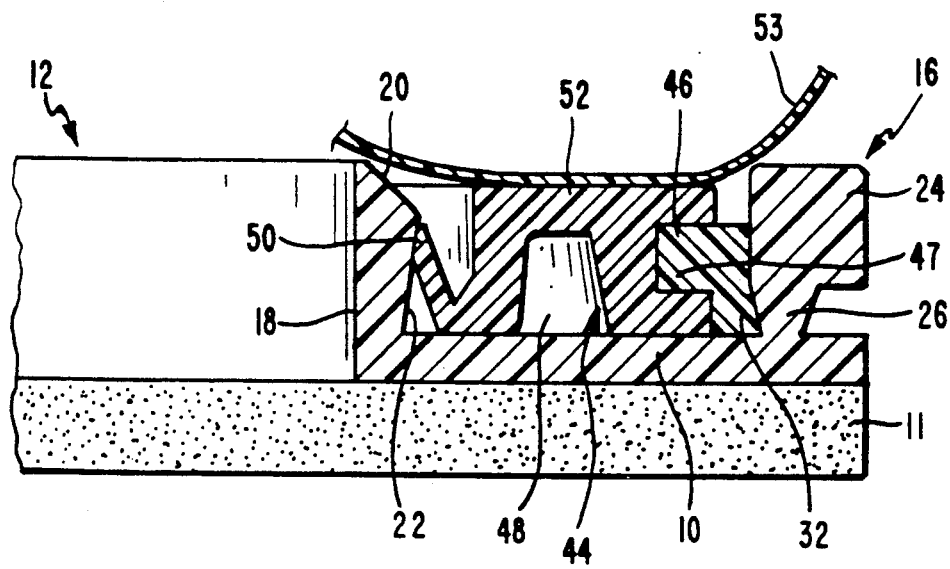
FIG. 9 is a fragmentary section through the coupling when assembled before locking.

Having made the seal in this way (see FIG. 9), locking is achieved by rotating the locking ring so that the elongated portions 39 of the spurs 36 hook under and guide the locking projections 16 into the slots 38, until the pips 28 on the projections locate in the recesses 42 on the spurs. To achieve this, depending on the orientation of the bag, the locking ring and the seal ring and the attached bag may rotate as one unit relative to the body side coupling, or the seal ring and the attached bag may be kept stationary while the locking ring is rotated relative to the body side coupling 10 to engage the spurs 36 on the locking ring with the projections 16 on the body side coupling. Initial engagement of the spurs with the projections is assisted by the tapered lead-in on the portions 39. The complimentary wedge shapes at 26 and 43 of the projections and the slots, respectively, and the fact that the projections are engaged on both sides of the V-portions 26 when locked ensure that the projections cannot lift out of engagement with the slots during normal flexing movement of coupling encountered during use.

The coupling is relatively thin when assembled and the locking ring and projections do not add to the overall thickness of the coupling which, in the illustrated example, is dictated by the length of the chute 12 alone.

What we claim is:

1. An ostomy bag coupling including a body side coupling which includes first seal means surrounding an inlet or stoma aperture and body side support means supporting and integrally formed with said first seal means, and a bag side coupling which includes second seal means for cooperating with said first seal means and a bag side support means associated with said second seal means, said bag side support means including, at a plurality of locations spaced therearound, walls extending radially in the plane of the bag side support means, said walls defining respective generally arcuately extending slots, each of which lies in the plane of its respective radially extending wall and is open at one end and closed at the other and has sidewalls defining the sides of the slots, and the body side support means including a plurality of spaced projections for being releasably received in said slots, whereby on engagement of said first and second seal means and subsequent relative rotation of said support means in the appropriate sense, said projections are received in respective slots thereby releasably locking the coupling against separating movement.

2. An ostomy bag coupling according to claim 1 wherein the bag side support means comprises a locking ring and the associated seal means are separately formed and the slots are defined by respective spurs which extend from the locking ring in a generally circumferential direction, spaced from the outer peripheral surface of said locking ring.

3. An ostomy bag coupling according to claim 2 wherein the free ends of the spurs are tapered to assist engagement of the projections in the respective slots.

4. An ostomy bag coupling according to claim 2 wherein the seal means is formed of an EVA material.

5. An ostomy bag coupling according to claim 2 wherein the locking ring is formed of an engineering plastic.

6. An ostomy bag coupling according to claim 5 wherein at least one of said slots and projections include complimentary detent means.

7. An ostomy bag coupling according to claim 2 wherein one of the seal means includes an inwardly directed resiliently deformable rib and the other seal means includes a chute of generally hollow cylindrical form having an outer peripheral surface for being sealingly engaged by said inwardly directed rib.

8. An ostomy bag coupling according to claim 7 wherein the outer peripheral surface of said chute includes a frusto-conical convergent portion adjacent a flange portion of said seal means.

9. An ostomy bag coupling according to claim 7 wherein said body side locking ring and the associated seal means are capable of relative rotation.

10. An ostomy bag coupling according to claim 2 wherein said body side locking ring and the associated seal means are capable of relative rotation.

11. An ostomy bag coupling according to claim 2 wherein the body side seal means comprises a chute of generally hollow cylindrical form having an outer peripheral surface and the bag side seal means comprises an inwardly directed resiliently deformable rib for sealing engagement with said outer peripheral surface.

12. An ostomy bag coupling according to claim 11 wherein the outer peripheral surface of said chute includes a frusto-conical convergent portion adjacent a flange portion of said seal means.

13. An ostomy bag coupling according to claim 12 wherein said body side projections are spaced apart from said chute and said bag side coupling is positioned intermediate said outer peripheral surface of said chute and an inner surface of said projections except that said slots engage said projections on both an outside surface and said inner surface of said projections when said bag side and body side couplings are locked.

14. An ostomy bag coupling according to claim 13 wherein the walls of each of said slots converge towards a flange portion of said body side coupling and the inner and outer surfaces of the associated projection is complementary shaped.

15. An ostomy bag coupling including a body side coupling which includes first seal means surrounding an inlet or stoma aperture and body side support means supporting and integrally formed with said first seal means, an a bag side coupling which includes second seal means for cooperating with said first seal means and a bag side support means associated with said second seal means, said bag side support means including, at a plurality of locations spaced therearound, walls extending radially in the plane of the bag side support means, said walls defining respective generally arcuately extending slots, each of which lies in the plane of its respective radially extending wall and is open at one end and closed at the other and has sidewalls defining the sides of the slots, and the other body side means including a plurality of spaced projections for being releasably received in said slots, wherein the sidewalls of each of said slots on said one support means converge axially towards a flange portion of the other support means and each associated projection is generally complementarily shaped to the slot, whereby on engagement of said first and second seal means and subsequent relative rotation of said support means in the appropriate sense, said projections are received in respective slots thereby releasably locking the coupling against separating movement.

16. An ostomy bag coupling including a body side coupling which includes first seal means surrounding an inlet or stoma aperture and body side support means supporting said first seal means, and a bag side coupling which includes second seal means for cooperating with said first seal means and a bag side support means associated with said second seal means, said bag side support means including, at a plurality of locations spaced therearound, walls extending radially in the plane of the bag side support means, said walls defining respective generally arcuately extending slots, each of which lies in the plane of its respective radially extending wall and is open at one end and closed at the other and has sidewalls defining the sides of the slots, and the body side support means including a plurality of spaced projections for being releasably received in said slots, wherein the sidewalls of each of said slots on said one support means converge axially towards a flange portion of the other support means and each associated projection is generally complementarily shaped to the slot and at least one of said slots and projections include complementary detent members, whereby on engagement of said first and second seal means and subsequent relative rotation of said support means in the appropriate sense, said projections are received is respective slots thereby releasably locking the coupling against separating movement.

17. An ostomy bag coupling including a body side coupling which includes first seal means surrounding an inlet or stoma aperture and body side support means supporting said first seal means, and a bag side coupling which includes second seal means for cooperating with said first seal means and a bag side support means associated with said second seal means, said body side and bag side support means being in contact or closely separated when the body side coupling is coupled to the bag side coupling, one of said body side and bag side support means including, at a plurality of locations spaced therearound, walls extending radially in the plane of the body side or bag side support means, as the case may be, said walls defining respective generally arcuately extending slots, each of which lies in the plane of its respective radially extending wall and is open at one end and closed at the other and has sidewalls defining the sides of the slots, and the other support means including a plurality of spaced projections for being releasably received in said slots, whereby on engagement of said first and second seal means and subsequent relative rotation of said support means in the appropriate sense, said projections are received in respective slots thereby releasably locking the coupling against separating movement.

18. An ostomy bag coupling according to claim 17 wherein one of the seal means includes an inwardly directed resiliently deformable rib and the other seal means includes a chute of generally hollow cylindrical form having an outer peripheral surface for being sealingly engaged by said inwardly directed rib.

19. An ostomy bag coupling according to claim 17 wherein the seal means of said bag side coupling is secured to the ostomy bag around an inlet aperture thereof.

* * * * *